United States Patent [19]

Dalla Betta et al.

[11] Patent Number: 5,338,515
[45] Date of Patent: Aug. 16, 1994

[54] $SO_2$ SENSOR

[75] Inventors: Ralph A. Dalla Betta, Mountain View; David R. Sheridan, Menlo Park, both of Calif.

[73] Assignee: Catalytica, Inc., Mountain View, Calif.

[21] Appl. No.: 569,066

[22] Filed: Aug. 17, 1990

[51] Int. Cl.$^5$ .................. G01N 31/10; G01N 25/20
[52] U.S. Cl. ............................. 422/95; 422/51;
422/83; 422/98; 436/122; 436/119; 436/123;
436/147; 436/149; 436/157; 436/159; 23/293 S
[58] Field of Search .............. 422/83, 94, 95, 98,
422/51; 436/119, 122, 123, 106, 118, 147, 149,
157, 159, 160; 73/23.23, 31.05; 23/293 S

[56] References Cited

U.S. PATENT DOCUMENTS

| | | | |
|---|---|---|---|
| 2,751,281 | 6/1956 | Cohn | 23/255 |
| 3,488,155 | 1/1970 | Ayers | 23/232 |
| 3,537,823 | 11/1970 | Innes | 23/232 |
| 3,547,587 | 12/1970 | Innes | 23/232 |
| 3,607,084 | 9/1971 | Mackey et al. | 23/232 |
| 3,838,969 | 10/1974 | Dugan | 436/115 |
| 4,063,898 | 12/1977 | Fisher | 422/94 |
| 4,129,848 | 12/1978 | Frank et al. | 338/308 |
| 4,141,955 | 2/1979 | Obiaya | 422/95 |
| 4,170,455 | 10/1979 | Henrie | 23/232 R |
| 4,343,768 | 8/1982 | Kimura | 422/97 |
| 4,355,056 | 10/1982 | Dalla Betta et al. | 427/126.4 |
| 4,401,763 | 8/1983 | Itoh | 436/115 |
| 4,647,777 | 3/1987 | Meyer | 250/339 |
| 4,705,669 | 11/1987 | Tsuji et al. | 422/93 |
| 4,778,764 | 10/1988 | Fine | 436/116 |
| 4,834,962 | 5/1989 | Ludwig | 422/171 X |
| 4,836,012 | 6/1989 | Doty et al. | 73/23 |
| 4,861,979 | 8/1989 | Tardy et al. | 250/227 |

*Primary Examiner*—Jill A. Johnston
*Assistant Examiner*—Long V. Le
*Attorney, Agent, or Firm*—Morrison & Foerster

[57] ABSTRACT

This invention is a process for detecting low concentration levels of sulfur oxides ($SO_2$) in a flowing gas stream (typically a combustion exhaust gas stream) and a catalytic $SO_2$ sensor system which may be used in that process.

14 Claims, 2 Drawing Sheets

$SO_2$ SENSOR

FIELD OF THE INVENTION

This invention is a process for detecting low concentration levels of sulfur oxides ($SO_2$) in a flowing gas stream (typically a combustion exhaust gas stream) and a catalytic $SO_2$ sensor system which may be used in that process.

BACKGROUND OF THE INVENTION

Exhaust gases produced by burning fuels using air as the source of oxidant typically contain small but significant amounts of various sulfur oxides (usually $SO_2$ or $SO_3$). $SO_2$ is a participant in the photochemical reaction creating modern "smog" and, therefore, is undesirable.

There are a number of ways in which the $SO_2$ may be removed or treated; however, each such process strongly benefits from use of an accurate monitor for detecting low levels of $SO_2$. However, there are few low level $SO_2$ sensors available which are practically suitable for inclusion in closed-loop controllers. Many of the prior measurement devices lack sensitivity. An ability to measure $SO_2$ content in combustion gases at levels below 150 ppm with some accuracy is desireable.

One $SO_2$ measuring procedure involves the use of an infrared beam, detector, and a comparator chamber. In U.S. Pat. No. 4,647,777 to Meyer a beam of infrared light is passed through a gas sample and into a selective infrared detector. The beam is split and one portion passes through a chamber containing a fluid which absorbs the spectral wavelengths of the selected gas. The two beams are compared and the difference between the two beams gives an indication of the amount of selected gas in the sample.

U.S. Pat. No. 4,836,012 to Doty et al. shows a semiconductor device made up of a photovoltic cell which, upon exposure to light, develops a voltage or current which varies as a function of the type of gas sorbed. The device requires a "thin light-transmitting gas-absorbing metal Schottkey layer having electrical properties which vary with the type of gas sorbed". Detection of CO, hydrocarbon, water vapor, etc. is suggested; detection of $SO_2$ is not.

The U.S. Pat. No. 4,778,764 to Fine describes a device and a process in which a sample is injected with a solvent into a chromatographic column to separate the various materials present in the sample. The output of the column is then burned in the presence of a variety of detectors for one or more of $NO_x$, $SO_2$, $CO_2$, and halogens.

None of the above disclosures suggest a process or an apparatus in which a catalytic sensor element is used to detect the presence of a gaseous component.

The concept of using the temperature rise of a gas as it reacts in passing through a catalyst bed as an indicator of the content of a component of that gaseous mixture has been shown. For instance, in U.S. Pat. No. 2,751,281 to Cohen, a method is taught for measuring low concentrations of gas impurities (such as oxygen) in the range of 0.0001% to 0.001%. A thermocouple is placed such that a cold reference junction is on the upstream side of a bed of catalyst and the hot junction is placed on the downstream side of that bed. As the gas flows across the catalyst, the temperature of the gas rises, is measured, and the content of the incoming gas calculated.

U.S. Pat. No. 3,488,155 to Ayers shows a similar process in which the temperature on each side of a hydrogenation catalyst bed is measured during the flow of a gas containing hydrogen. The temperature difference is related to the hydrogen content of the incoming gas stream.

The U.S. Pat. No. 3,537,823 to Ines suggests a process for measuring the quantity of "smog forming hydrocarbons in a gas sample" by measuring the temperature rise in an oxidation catalyst bed. Moreover, a related process is found in U.S. Pat. No. 3,547,587 also to Ines.

U.S. Pat. No. 3,607,084 to Mackey et al. teaches a process for the measurement of a combustible gas content by locating a pair of wires in a small chamber containing a volume of gas with combustibles therein. One wire is coated with a catalytic mixture of a metal oxide and a powdered metal of the platinum group and the other is apparently uncoated. Electrical power supplies heat to both wires. The difference in resistance caused by the change in temperature of the wire coated with the catalytic mixture provides an indicator of the amount of combustibles in that gas chamber.

U.S. Pat. No. 4,170,455 to Henrie also suggests a method for the monitoring of the hydrogen or oxygen content of a gas stream by measuring the temperature upstream and downstream of an oxidation catalyst.

U.S. Pat. No. 4,343,768 to Kimura shows a gas detector formed using semiconductor technology. The detector uses dual heating elements over a channel adapted for gas flow. One of the heating elements is coated with a "catalytic or gas responsive film" which may be platinum or palladium. The increase in the temperature of the catalytic film is detected in terms of the variation in electrical resistance in the content of the gas stream calculated.

Finally, U.S. Pat. No. 4,355,056 to Dalla Betta et al. suggests a differential thermocouple combustible sensor in which one junction of the thermocouple is catalytically coated and the other junction is not. The gas stream contains such gases as carbon monoxide and hydrogen and is said to be "insensitive to contaminants such as $SO_2$ and NO".

None of these disclosures suggests a process for catalytically oxidizing all of the oxidizable materials except $SO_2$ in the gas stream to be measured and then oxidizing the $SO_2$ to $SO_3$ on a separate catalytic element.

This invention is a sensor assembly having a catalytic oxidation preconverter and a functionally specific configuration of a catalytic sensor element having an integral thermally isolated temperature measuring device, e.g., a thermistor or RTD. Another portion of the sensor may be a temperature reference element.

This sensor configuration, particularly in conjunction with the inventive process, permits fast resolution of the $SO_2$ content of the gas passing by the sensor to a high degree of accuracy and is insensitive to interference from other gas components in the measured stream.

SUMMARY OF THE INVENTION

As was noted above, the invention is a $SO_2$ sensor and a process for using the sensor to measure $SO_2$ in a flowing gas stream.

The sensor assembly itself may be made up of three major discrete functional portions: a catalytic oxidation preconverter, a catalytic sensor element, and a reference sensor element.

The catalytic oxidation preconverter is a catalytic oxidation stage in which most oxidizable materials other than $SO_2$ in the stream to be measured, e.g., $NO_x$, CO, amines, NH$_3$, etc., are oxidized to their most highly oxidized forms.

The catalytic sensor element and the reference sensor element (when placed in the gas stream) are downstream from the catalytic oxidation preconverter. The catalytic sensor element has on its outside periphery a catalyst suitable for oxidizing SO$_2$ to SO$_3$ in thermal contact is a temperature measuring device. Both are generally thermally isolated from the operating environment and each other. The catalyst is selected and placed about the temperature measuring device so that the SO$_2$ in the gas stream is oxidized to SO$_3$ on the catalyst surface with oxygen. The temperature measuring device may be a device such as a resistance temperature detector (RTD) a thermistor, or a thermocouple which detects the small temperature rise which occurs due to the SO$_2$ oxidation reaction taking place on the catalyst. The catalyst and temperature measuring device should be in close (ideally, contiguous) physical proximity and constructed in such a way that they retain most of the heat of reaction produced by the reduction reaction. The heat of reaction should then cause only the temperature of the temperature measuring device in communication with the catalyst to rise. Baffles or shields may be used in the vicinity of the catalytic sensor element to lessen the amount of heat which is radiated away from that catalytic element either to the reference element (if one is used) or to other surrounding portions of a sensor instrument.

The temperature of the catalytic sensor element is obviously converted to an electrically measurable quantity (voltage, resistance, etc.) by the temperature measuring device and is compared to the analogous quantity from the reference element. The difference in temperature is proportional to the SO$_2$ concentration in the measured gas. Calibration of the sensor element assembly, as with all good instrumentation, is both desireable and necessary.

DESCRIPTION OF THE INVENTION

The invention is both a SO$_2$ sensor capable of measuring low SO$_2$ concentrations and a process for detecting and measuring SO$_2$ in a flowing gas stream using that sensor.

Figure 1:
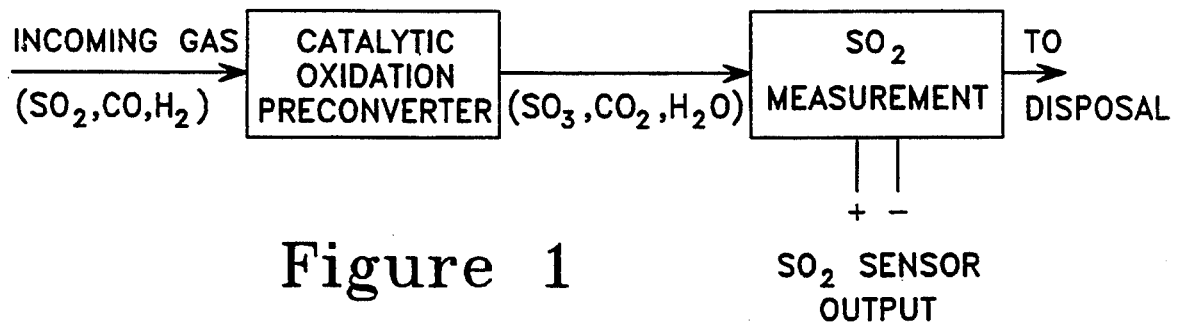
FIG. 1 is a block diagram of the inventive device.

As is shown in FIG. 1, the incoming gas may contain a variety of components. In a combustion gas stream, components such as CO, H$_2$, HCN, amines, etc., may be present in addition to SO$_2$. Some N$_2$ and O$_2$ are usually present as components of the inlet air which passes unreacted through the combustion process. In the catalytic oxidation preconverter, a catalytic body oxidizes the other components to forms which are not oxidizable in the later SO$_2$ measurement step. For instance, any CO present is oxidized to CO$_2$ in the preconverter step. The CO$_2$ is not oxidizable at the catalytic SO$_2$ sensor.

The gas containing the oxidized gas components is then passed to the SO$_2$ measurement stage where, using an oxidant such as O$_2$, the SO$_2$ is oxidized to SO$_3$ on the catalytic sensor element. The temperature of the catalytic sensor element rises due to the oxidation reaction. The temperature rise is related to the amount of SO$_2$ present in the gas stream which is reacted to SO$_3$ on the catalytic sensor element. The electrical output from the catalytic sensor element is, therefore, related to the SO$_2$ content of the measured gas.

CATALYTIC OXIDATION PRECONVERTER

The preconverter is a simple catalyst bed or monolith utilizing a catalyst which is very active at what may be a comparatively lower temperature, to oxidize the components of the gas stream which (other than SO$_2$) can be oxidized. We have found that many of the Group VIII noble metals, e.g., Ru, Rh, Pd, Os, Ir, and their mixtures, are especially suitable as catalysts in this stage. Platinum is not suitable since it oxidizes SO$_2$ to SO$_3$. Rhodium, palladium, and particularly their mixtures are especially preferred. These metals are capable of oxidizing the non-SO$_2$ (and nonhydrocarbon) oxidizable materials at temperatures between 300° C. and 500° C., preferably between 400° C. and 500° C.

The amount of Group VIII noble metal present in the catalyst will be at least an effective amount and will depend, for example, on required catalyst activity, ease of uniform dispersion, and the type of substrate utilized. Generally, however, the level of metal present will range from about 0.01% to 3.5% and, more preferably, 0.01% to 2.5%. Furthermore, the amount of metal present is generally from 0.1% to 2.0% by weight of the catalyst if a packed bed is used and from about 0.01% to 6% by weight if a monolithic substrate having high space velocity through its channels is chosen.

The noted Group VIII noble metals may be introduced onto the substrate by impregnation, carbonyl decomposition, adsorption from the gaseous phase, introduction during substrate synthesis, and adsorption of metal vapor; the preferred technique is impregnation.

Figure 2:
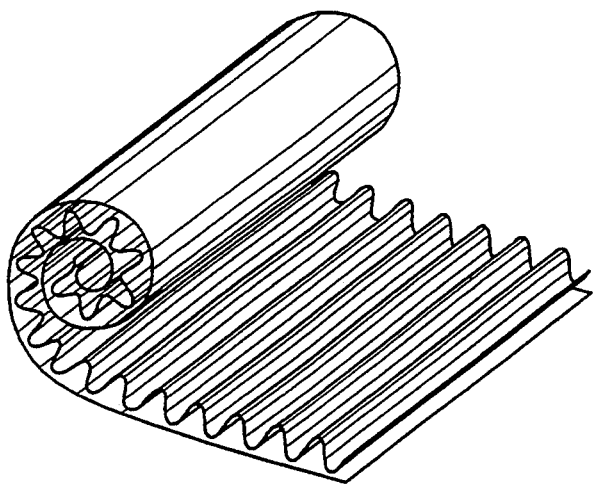
FIG. 2 is a catalyst support suitable in the catalytic oxidative preconverter.

FIG. 2 shows a monolithic catalyst substrate structure suitable as the support for the catalytic oxidation preconverter. It may comprise any suitable support material. If a ceramic, cordierite is desirable. If a metallic substrate, alumina containing steel is desired. It may be alumina, bentonite clay, diatomaceous earth, a zeolite, silica, activated carbon, magnesia, boria, titania, silica-alumina, or the like suitably pressed, molded, or otherwise made into an adherent monolith. The support should have a surface area greater than about 50 m$^2$/g, preferably from about 100 m$^2$/g to 300 m$^2$/g. The monolith is desirable in that it typically has a relatively low pressure drop as gas flows through it. On the other hand, because of the high velocity of the gas through the monolith, the specific amount of catalyst metal needed may be larger. Most preferable is a low surface metallic support made from corrugations of an alumina-containing steel. Such materials are typically used in automotive catalytic converters and are readily available. The metallic support should be coated with a wash coat of a high surface area material, e.g., a slurry of an alumina, dried to produce an adherent support, and calcined to form a high surface area support. The catalytic material may then be added as noted above.

Conversely, the catalyst support may be in the form of a packed bed of granules, balls, Pall rings, etc., and made from the same materials noted above. A packed bed typically requires less catalyst than required for a monolith since the space velocity of the gas is much lower than for a monolith.

SO₂ Sensor Assembly

The sensor assembly is made up of two major components which are critical to its operation (the catalytic sensor element and the reference element) and a number of other components which in some configurations may lead ease of operation and reliability to its use.

First, the catalytic sensor element is made up of a catalyst and a temperature measuring device.

Figure 3:
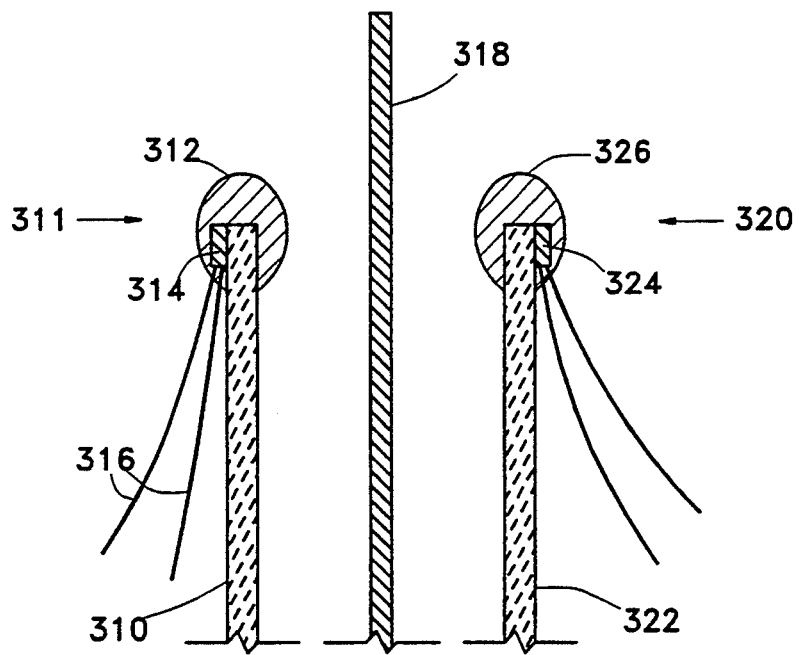
FIG. 3 depicts a sensor set useful in the inventive sensor device.

FIG. 3 shows a cutaway schematic depiction of a catalytic sensor element (311) and a reference element (320) within the scope of the invention. This variation of the inventive device uses a thermally insulating support or substrate (310 and 322) as a portion of the element. These supports allow the respective elements to be used as probes or fingers extending into a flowing gas stream. The substrate should be a thermally insulating support having sufficient mechanical strength to support the catalyst and temperature measuring devices in the flowing stream. The substrate (310) may be ceramic or may be a ceramic coating on a metallic support. Suitable ceramic materials include fired kaolin, alumina, silica-alumina, and silica. Ceramic materials which are typically used as catalyst supports are also suitable for the substrate providing that they possess the necessary mechanical strength to withstand the temperature cycling steps as the device is turned on and off, the lengthy times the element will spend at the desired operating temperature, and the normal mechanical shocks endured during installation and operation. These ceramic materials are also suitable because of the variety of procedures available for making the catalytic material (312) adhere to the ceramic substrate (310).

The temperature measuring device (314) may be any of a variety of devices which produce a variation in a measurable physical quantity, e.g., voltage or resistance, as the temperature of the device changes. A bimetallic thermocouple, particularly a chromel-alumel thermocouple, may be cemented to the substrate (310) using known and available ceramic cements. The sensitivity of the chosen temperature measuring device must match the sensitivity of the resulting analyzer. For instance, as a rule of thumb, thermocouples may be accurate only to a ±1° F. In measuring low levels of SO₂, such as levels below 60 ppm, a more sensitive temperature measuring device, such as an RTD, may be necessary. The face of the temperature measuring device away from the support should be substantially free of gas barriers so that the gas to be measured contacts the catalytic surface (312). The temperature measuring device may be a thermistor chosen for appropriate sensitivity in the proper temperature range. If a ceramic substrate (310) is selected, the temperature measuring device need not be discrete and assembled onto the substrate but may instead be made directly on the ceramic surface by known technologies. See, for instance, the procedure for creating thermistors on a ceramic substrate shown in U.S. Pat. No. 4,129,848 to Franc et al. The leads (316) from the temperature measuring device allow the variable physical quantity corresponding to temperatures of the device to be measured. The temperature measuring devices may be placed within the substrate; the substrate may be formed from a thermowell.

Finally, the catalyst layer (312) may be fairly thin to promote conduction of the heat of reaction produced at the surface to the temperature measuring device (314) and to reduce the thermal mass of the catalyst sensor element. There are a number of suitable catalysts for the following reactions:

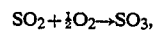

Preferred catalysts include Group VIII noble metal catalysts, such as platinum, palladium, and rhodium and mixtures; Group VB metal oxides, such as vanadium oxides; and Group VIII metal oxides, such as iron oxide.

Because of the desirability of producing a catalyst layer of minimal thickness, the catalyst or catalyst precursor may be applied using a liquid having little or no solids content. For instance, a catalyst precursor of a dissolved or chelated catalytic metal, e.g., an acetylacetonate, in a suitable solvent, e.g., dimethyl formamide, may be used to impregnate the ceramic surface. Once dipped, sprayed as a wash coat, or otherwise impregnated, the element may be calcined in oxygen or air to produce an active catalyst.

A particularly suitable procedure for applying the catalyst to the catalytic sensor element is via use of metal salts of the appropriate catalytic metal to the element support. The salt, preferably a nitrate, sulfate, or chloride, is applied as a saturated aqueous solution to maximize the available catalytic metal to the element.

In some applications a baffle or shield (318) is desired to minimize radiant and convective heat loss from the catalytic surface (312) to the reference element or other cooler portion of the sensor assembly.

Second, the reference element (320) may be similar in design to the catalytic element (311) except that the catalyst layer is excluded and an optional protective layer (326) for the temperature measuring device may be added.

The reference element (320) is intended to provide a comparative temperature measurement which temperature is that of the non-reacted gas flowing past the reference element or catalyst sensor element. The reference element may, in fact, be an arbitrarily selected fixed value element if the temperature of the gas and the environment "seen" by the catalytic sensor element can be carefully controlled. For instance, if the catalytic sensor element is placed in an iso-thermal environment such that in essence the surrounding temperature is controlled rather than measured, a precision resistor (if the temperature measuring device for the catalytic sensor element is an RTD or a thermistor) or a voltage source (if the temperature measuring device is a thermocouple) may be used instead of a reference element which measures local temperature.

Neither element is directly heated using current flowing through the sensing element, e.g., resistance heating.

In FIG. 3 the reference element (320) is made up of a mechanical support, a temperature measuring device, and an optional protection layer. The variation shown in FIG. 3 includes a mechanical support (322) similar in function support (310). The temperature measuring device (324) is mounted on the support or, as with the catalytic element, may be produced integrally with the ceramic surface of the support if, of course, the support is ceramic. The protective coating (326) is optional depending upon the corrosivity of the gas stream measured and the reactivity of the temperature measuring device employed.

The optional protective coating (326) on the reference element may be of alumina, silica, epoxide resins, carbon, or other heat conducting material. The coating is to protect the temperature measuring device (324) from corrosive elements, e.g., $SO_2$, $SO_3$, $NO_2$, $H_2O$, etc., in the gas stream but should not interfere in the reference element's task of measuring local temperature. Additionally, the protective coating (326) improves the match of the thermal mass of the reference element (320) and the catalytic sensor element (312). If the catalytic sensor element (311) were to be coated with a catalyst and the reference element were not, the thermal mass of the reference element would be much less and would respond to changes in ambient flowing gas temperature much more quickly than the catalytic sensor element. Such a response difference clearly could cause errors in the $NO_x$ measurements. Further, the protective coating (326) provides cross-sectional and surface areas of the reference element (320) relatively similar to those of the catalytic sensor element (311). Similarity in those areas results in similar convective heat transfer loads.

The reference element (320) desirably is designed so that the configuration of the gas as it flows past is similar to the flow past the catalytic sensor element (311). Said another way, the aerodynamic shapes of the two elements should be similar. The two elements ideally should be placed in similar and representative flow regions in the measured gas, i.e., both may be placed in a turbulent flow region of the gas so that the gas measured is equally representative. For instance, placement of one element in a non-turbulent flow region and another in a turbulent flow region should be avoided in that it causes unequal measurements of the gas stream's incoming temperature.

The two elements should be optimized in shape and materials of construction to minimize heat loss via conduction or radiation. Support materials should be selected so that the heat of reaction on the catalytic coating (312) of the catalyst sensor element (311) is maintained at the temperature measuring device (314). The elements should be as small as is practically possible so to permit rapid response to temperature and $NO_x$ content. Use of small elements also results generally in less radiation heat loss to the surroundings. The two elements should have similar thermal mass and should, as much as is possible, have similar heat transfer characteristics. The catalytic sensor and reference elements need not be in the configuration shown in FIG. 3. Other variations are suitable.

The catalytic oxidation preconverter and the catalytic sensor elements and reference elements shown in FIG. 1 are best employed in a sensor assembly in which the flow rate of the gas being measured and its temperature are carefully controlled.

The signals emanating from each of the temperature measuring devices in the catalyst element and the reference element are compared using well-known circuitry (wheatstone bridges, differential amplifiers, etc.) and the $SO_2$ content of the gas stream measured via calibration. Because of the linearity of the inventive assembly, the $SO_2$ concentration may be measured directly after such calibration.

Figure 4:
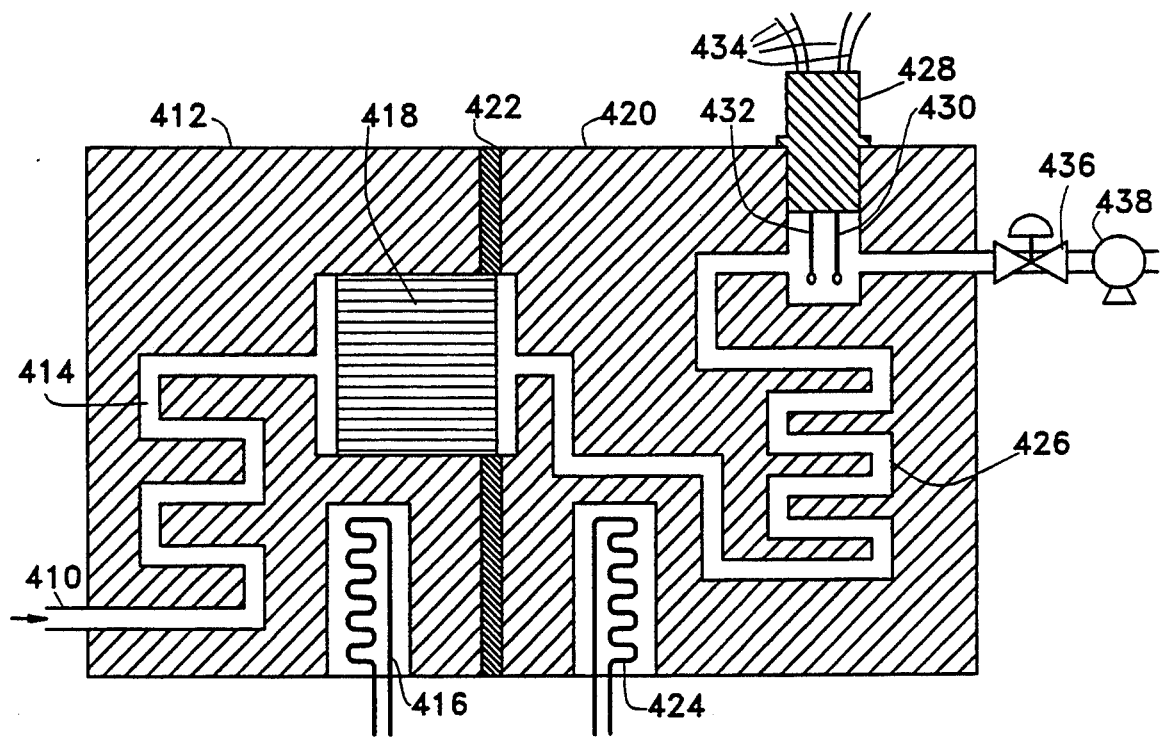
FIG. 4 is a simplified diagram (cross section) of an integrated SO$_2$ sensor device according to the present invention.

The catalytic oxidation preconverter and the $SO_2$ sensor assembly may be assembled in the fashion shown in FIG. 4.

The gas to be sampled is drawn in through sample port (410) from the combustion gas stack which disposes of that combustion gas. The sample gas passes into a temperature controlled heat exchanger block (412) through a labyrinthine heat exchanger section (414) which has several functions but mostly provides an isothermal heat source which brings the sample gas mixture up to the desired operating range. The block may contain one or more heater elements (416). A variation would be a heater external to the block which maintains the block at the desired temperature. In any event, the sample gas mixture passes through the heat exchange surfaces which may be in the labyrinthine form (414) shown in FIG. 4. After heating to the operating temperature, the gas passes to the catalytic oxidation preconverter catalyst element (418) of the form discussed above with regard to FIG. 2. The operating temperature of the catalytic oxidation preconverter element (418) desirably is between 400° C. and 500° C., preferably between 425° C. and 475° C. The oxidation preconverter element (418) may be made using conventional substances such as a ceramic, ceramic coated metal, or metal support. Ceramic materials which are suitable for the substrate include alumina, silica, fired kaolin, silica-alumina, etc. Other refractive metal oxides are also suitable.

The appropriate catalytic metals for the oxidation preconverter are discussed above.

Oxidizable components in the gas to be measured are oxidized in the oxidation preconverter catalyst (418) and pass out into a second temperature controlled heat exchanger block (420). The first heat exchanger block (412) and the second heat exchanger block (420) may be separated by an insulating gasket (422). In this way, the temperature of the gas in the oxidation preconverter catalyst (418) may be controlled independently of the temperature downstream.

The temperature of the second heat exchanger block (420) may be controlled using one or more heater elements (424). The gas passes through the labyrinthine heat exchanger path (426) to reach a $SO_2$ sensor assembly (428) such as shown above in FIG. 3. The $SO_2$ element assembly contains both a catalytic sensor element (430) and a reference element (432). The signal leads (434) from the temperature measuring devices in the element assembly are available for electronic processing to produce a signal indicative of the $SO_2$ content. The thus measured gas flow then exits the block (420). The flow rate of the sampled gas through the temperature controlled heat exchanger blocks (412 and 420) may be controlled by control valve (436) and vacuum pump (438). The control valve (436) may be some other suitable flow control device, e.g., orifice, etc. The pump (438) may be another suitable suction device such as an eductor, aspirator, or thermal siphon.

The sample gas may then be disposed of.

Non-essential portions of the $SO_2$ sensor which would nonetheless be apparent to an ordinary worker in this art have been omitted for clarity of discussion. For instance, the line supplying sample gas to the sensor apparatus should be maintained above the dew point to prevent problems with condensation and consequent loss of device accuracy. Similarly, a filter may be installed to remove particulates before the gas reaches the sensor element assembly.

SO₂ Detection Process

The process follows use of the SO₂ detector discussed above very closely.

A sample gas stream containing SO₂ is brought to a suitable temperature for a catalytic oxidation preconverter of the type discussed above. The oxidizable components in the gas stream (except SO₂) are substantially oxidized using excess $O_2$ in the sample stream.

The gas exiting the catalytic oxidation preconverter containing SO₂ and the oxidized components ($NO_2$, $CO_2$, etc.) is then brought to a suitable temperature and passed to a SO₂ sensor assembly (also discussed in detail above). The catalytic material may be selected from those discussed above. The catalyst will cause the oxidant exothermally to oxidize the $SO_2$ to $SO_3$ and to raise the temperature of the catalytic element. It is desirable that the $O_2$ concentration of the gas stream be appropriately constant since there is some $O_2$ sensitivity in the catalytic element. The increased temperature will be measured by the temperature sensing device producing a measurable output approximately proportional to the rise in temperature. The temperature sensing device may be a thermocouple suitable for the necessary sensitivity and temperature range. If a thermocouple is used in the temperature sensing device, the output from the device will be a voltage. If other devices are used, e.g., RTD or thermistors, the resistance of the device will vary with the temperature. An appropriate voltage would then be applied to the temperature measuring device and the resulting resistance detected. Temperature measuring devices based on optical operating principles are also known. One suitable optical temperature measuring device is found in U.S. Pat. No. 4,861,979.

The gas may also be passed over a reference element which comprises a temperature sensing device of the same type found in the catalytic sensor element. The temperature sensing device provides an output which is then compared to the output from the catalytic element and the difference in the element outputs determined. The SO₂ content is calculated from this difference in output between the elements.

EXAMPLES

The sensor and process have been described in detail above. The following examples show various aspects of the invention but are not to be considered as limiting the scope of the invention's disclosure.

EXAMPLE 1

This example shows the preparation of a catalytic oxidation preconverter catalyst in monolithic form suitable for use in this invention.

A monolithic cordierite (Corning) having 400 cells per square inch was cut into several square pieces having 10 cells×10 cells, all 1.5 inches long. The square samples were washed first in water and then in acetone and then calcined at 450° C. in air for one hour. The cells are square in cross section and run straight through the samples.

Since cordierite is dense and has a relatively low surface area, it was coated with a high surface area alumina. The alumina was applied in the form of a sol prepared by ball milling a mixture of alumina (Versal GH), water, $HNO_3$ (at pH=3.0) for about two days. The cordierite sample was dipped in the alumina sol and blown with a $N_2$ stream to remove excess solution. The coated support was dried and calcined. The alumina sol coating added about 7.0% to the weight of the support.

The calcined support was then dipped into a palladium chloride ($PdCl_4^2$) solution. The sample contained about 0.25% Pd after treatment with $H_2S$ (to set the palladium), drying, and calcining.

EXAMPLE 2

This example shows the preparation of a catalytic oxidation preconverter catalyst in packed bed form suitable for use in this invention.

A commercial support (Rhone-Polenc SCS100) of ⅛ diameter spheres made of gamma-alumina was ground down to a smaller diameter (16–32 mesh) appropriate for the catalyst bed desired. The ground alumina was hydrothermally treated in air and 10% steam at 620° C. to stabilize the alumina surface.

The treated alumina was impregnated with a platinum-rhodium solution containing a ratio (by weight) of Pt/Rh=0.67. The final catalyst contained about 0.35% metal.

The catalyst was loaded into a stainless steel tube (1.5 inches×0.5 inches diameter) and held in place by a screen and glass wool.

EXAMPLE 3

This example shows the preparation of a SO₂ catalytic sensor element using RTD's as the temperature measuring devices suitable for use in this invention.

The catalytic sensor element and the reference elements use a prepared ceramic tab about ¼ inch made by gluing a flat 100 ohm RTD. The two RTD tabs are suspended in a ¼ inch OD ceramic tube. The RTD tabs were then coated with an alumina so similar to that used in Example 1.

One of the tabs was then dipped repeatedly in a solution of chloroplatinic acid containing 0.16 gm Pt/gm solution. The dipping steps were interspersed with drying steps. Finally the platinum was stabilized in $H_2S$ and the sensor elements calcined at 500° C. for 1.5 hours.

The two tabs (one catalytic and one reference) were assembled into an insulated support such that they could be stably supported in the flowing gas stream of an SO₂ sensor unit.

EXAMPLE 4

This example shows the operation of the invention SO₂ sensor assembly upon a number of gases containing a variety of components such as CO, SO₂, and NO.

The total flow of gases through the sensor assembly was about 1000 sccm. The temperature of both the preconverter and the sensor was 450° C.

The catalyst in the oxidation preconverter was a Pt-Rh material similar to that prepared in Example 2. The sensor elements were similar to those described in Example 3 except that the element supports were ceramic coated stainless steel.

| Gas Composition to Preconverter* (ppm) | | | Corrected Sensor Output in MV |
|---|---|---|---|
| CO | SO₂ | NO | |
| 0 | 470 | 0 | 321.5 |
| 0 | 962 | 0 | 675.0 |
| 0 | 1458 | 0 | 1011.3 |
| 452 | 0 | 0 | 3.5 |
| 452 | 469 | 0 | 318.6 |
| 452 | 961 | 0 | 663.0 |
| 452 | 1456 | 0 | 991.5 |

-continued

| Gas Composition to Preconverter* (ppm) | | | Corrected Sensor Output in MV |
|---|---|---|---|
| CO | SO$_2$ | NO | |
| 0 | 0 | 477 | 28.9 |
| 0 | 471 | 479 | 345.6 |
| 0 | 963 | 479 | 696.8 |
| 0 | 1460 | 477 | 1034.5 |
| 452 | 0 | 478 | 29.8 |
| 452 | 470 | 477 | 337.3 |
| 452 | 962 | 477 | 682.2 |
| 452 | 1458 | 477 | 1007.4 |

*contained 1.2% H$_2$O and 9.86% O$_2$

Figure 5:
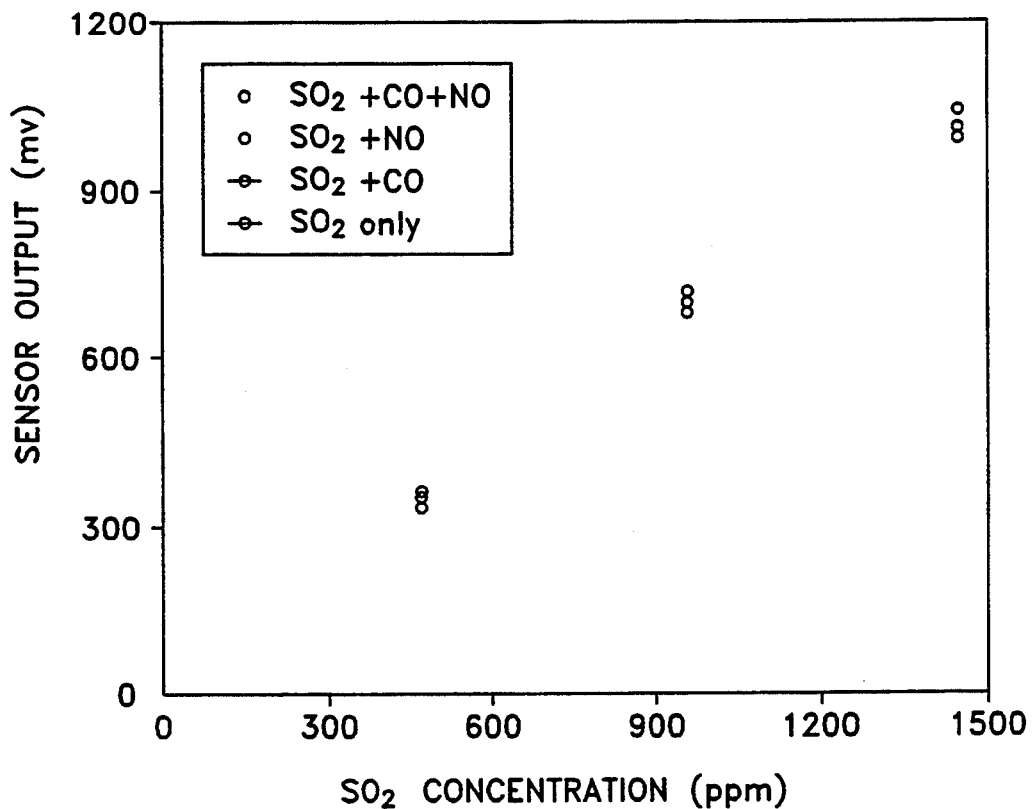
FIG. 5 is a graph of sensor output as a function of SO$_2$, NO, and hydrocarbon input to the sensor assembly.

These results are shown in FIG. 5. It should be clear that the presence of the oxidizable components CO and NO did not affect the operation of the SO$_2$ sensor downstream.

This invention has been disclosed both by description and by example. The examples are just examples and should not be used to limit the scope of the invention here claimed in any way. Additionally, it will be apparent to a reader having ordinary skill in this art that the variations and equivalents will be apparent and will operate in the same way in measuring SO$_2$ and yet be within the spirit of these claims.

We claim as our invention:

1. A device for measuring SO$_2$ concentration in a flowing gas stream comprising:
   a. an oxidation catalyst selected from the group consisting of Ru, Rh, Pd, Os, Ir, Group VIB metal oxides, and Group VIII metal oxides and adapted to oxidize oxidizable components of the flowing gas stream but not SO$_2$, said catalyst being situated to oxidize said oxidizable components in the flowing gas stream prior to contacting the flowing gas stream with a catalytic sensor element;
   b. a catalytic sensor element comprising a catalyst suitable for oxidizing SO$_2$ to SO$_3$ in the presence of oxygen and a temperature measuring device, where the catalyst is placed about as a layer over the temperature measuring device so that the catalyst is in physical and thermal contact with the temperature measuring device and where the catalyst is in contact with the flowing gas stream, and the heat produced by oxidizing SO$_2$ raises the temperature of the temperature measuring device substantially proportionally to the SO$_2$ concentration in the flowing gas stream;
   c. a reference element adapted to detect the ambient temperature of the flowing gas stream in the vicinity of the catalytic sensor element; and
   d. a flowing gas temperature controller for controlling the temperature of the flowing gas stream prior to its passage over the catalytic sensor element to operating temperature.

2. The device of claim 1 where the temperature measuring device of the catalytic sensor element is a resistance temperature detector.

3. The device of claim 1 where the temperature measuring device of the catalytic sensor device is a thermistor.

4. The device of claim 1 where the temperature measuring device of the catalytic sensor element is a thermocouple.

5. The device of claim 1 where the oxidation catalyst is selected from the group consisting of rhodium, palladium, and mixtures thereof.

6. The device of claim 1 where the catalyst on the catalytic sensor element comprises a metal selected from Group VIII noble metals.

7. The device of claim 6 where the catalyst or the catalytic sensor element comprises a metal selected from the group consisting of platinum, rhodium, palladium, and mixtures thereof.

8. The device of claim 1 where the reference element comprises a resistance temperature device in proximity to the catalytic sensor element.

9. The device of claim 1 where the reference element comprises a thermistor in proximity to the catalytic sensor element.

10. The device of claim 1 where the reference element comprises a thermocouple in proximity to the catalytic sensor element.

11. The device of claim 1 where the reference element is a resistor.

12. The device of claim 1 where the flowing gas temperature controller comprises a heat exchanger.

13. The device of claim 1 further comprising a heater for controlling the temperature of the flowing gas stream prior to its contact with the oxidation catalyst.

14. The device of claim 13 where the heater is a heat exchanger.

* * * * *